(12) United States Patent
Yates et al.

(10) Patent No.: US 10,408,768 B2
(45) Date of Patent: Sep. 10, 2019

(54) OPTICAL VIDEO MEASUREMENT SYSTEM HAVING INTERCHANGEABLE OPTICS

(71) Applicant: The L.S. Starrett Company, Athol, MA (US)

(72) Inventors: Robert Yates, Newport Beach, CA (US); Mark G. Arenal, Mission Viejo, CA (US); Robert D. Picone, Laguna Hills, CA (US)

(73) Assignee: THE L.S. STARRETT COMPANY, Athol, MA (US)

( * ) Notice: Subject to any disclaimer, the term of this patent is extended or adjusted under 35 U.S.C. 154(b) by 27 days.

(21) Appl. No.: 15/336,723

(22) Filed: Oct. 27, 2016

(65) Prior Publication Data

US 2017/0115234 A1 Apr. 27, 2017

Related U.S. Application Data

(60) Provisional application No. 62/246,990, filed on Oct. 27, 2015.

(51) Int. Cl.
  *G01N 21/88* (2006.01)
  *G03B 17/56* (2006.01)
  *H04N 5/225* (2006.01)

(52) U.S. Cl.
  CPC ....... *G01N 21/8851* (2013.01); *G03B 17/561* (2013.01); *H04N 5/2257* (2013.01); *G01N 2201/021* (2013.01)

(58) Field of Classification Search
  CPC ......... G01N 21/8851; G01N 2201/021; G06K 9/6202; G03B 17/14; G03B 17/561; H04N 5/2252; H04N 5/2253; H04N 5/2256
  USPC .......................................................... 348/86
  See application file for complete search history.

(56) References Cited

U.S. PATENT DOCUMENTS

| 2011/0013297 A1* | 1/2011 | Barnes | G02B 3/14 359/823 |
| 2015/0122143 A1* | 5/2015 | Hurd | F16M 11/18 104/165 |

* cited by examiner

*Primary Examiner* — Allen C Wong
(74) *Attorney, Agent, or Firm* — Grossman, Tucker, Perreault & Pfleger, PLLC

(57) ABSTRACT

A mounting assembly for an optical video system may include a platform having a track extending longitudinally along the platform. A camera mount may be slideably coupled to the track. A camera may be coupled to the camera mount. The camera may include a receptacle for engaging an interchangeable lens assembly. The mounting assembly for the optical video system may also include a biasing mechanism, wherein the biasing mechanism urges the camera mount along the track such that the receptacle engages the interchangeable lens assembly.

18 Claims, 11 Drawing Sheets

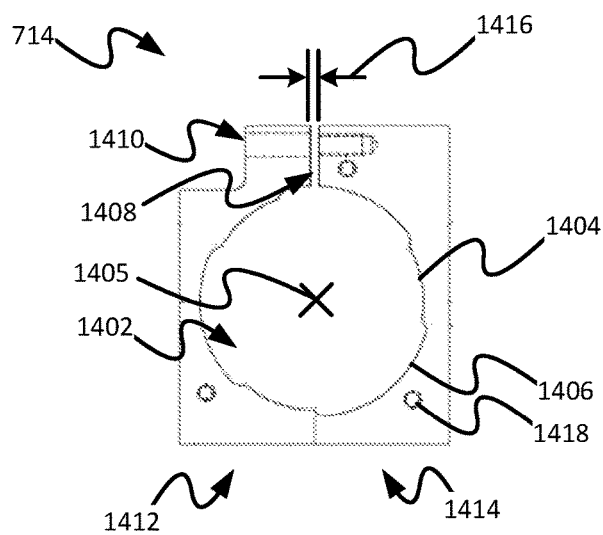
FIG. 14
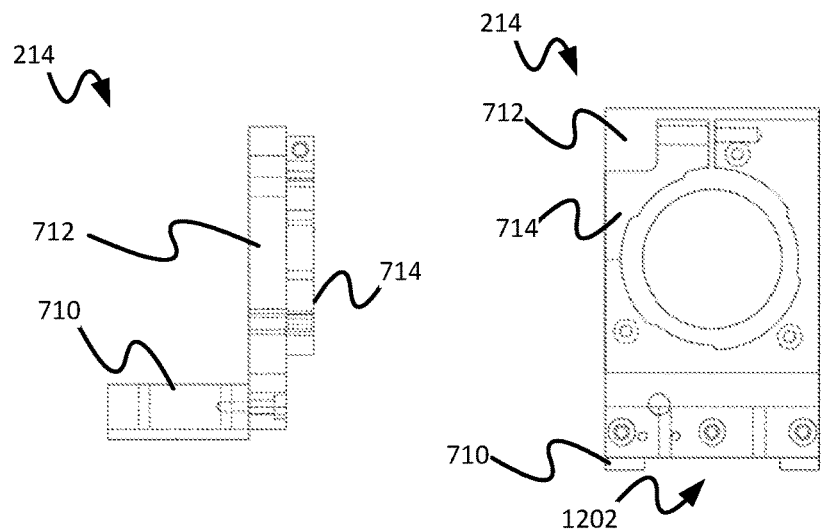
FIG. 15  FIG. 16

OPTICAL VIDEO MEASUREMENT SYSTEM HAVING INTERCHANGEABLE OPTICS

CROSS-REFERENCE TO RELATED APPLICATIONS

The present non-provisional application claims the benefit of U.S. Provisional Patent Application Ser. No. 62/246,990, filed Oct. 27, 2015, the entire disclosure of which is incorporated herein by reference.

FIELD

The present disclosure relates generally to measurement systems, and, more particularly, to a digital video measurement system having interchangeable telecentric video optics for imaging a manufactured part and measuring the manufactured part and/or comparing the manufactured part to an electronic design template and/or other representations of the manufactured part.

BACKGROUND

Optical metrology (i.e., the science of measurement) may be particularly important in the manufacturing industry. For example, certain manufactured parts may require specific dimensions (e.g., measurements). Although a design template used in the manufacturing of a part may include exact measurements, the actual dimensions of a manufactured part may deviate. As such, it is important that the actual dimensions of a manufactured part be measured or compared to a design template in order to ensure accuracy and consistency in the manufacturing process.

An optical video imaging platform (sometimes referred to as a comparator) is a device that applies the principles of optics to the inspection of manufactured parts. Generally, in a comparator, a magnified image of a manufactured part (such as a silhouette of the part) may be captured by a camera array and then projected upon a display screen and the dimensions and geometry of the part may be measured against prescribed limits. Generally, an optical comparator system includes one or more light sources, a support for the manufactured part, optics, and a display screen. The dimensions (e.g., measurements) of the manufactured part may be compared with the dimensions of a design template or to a calibrated linear or measurement standard to determine any inaccuracies and/or defects in the manufacturing of the part.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIG. 14 is a plan view of a camera clamp capable of being coupled to the camera support of FIG. 13, consistent with embodiments of the present disclosure;

FIG. 15 is a plan view of a camera mount including the base of FIG. 12, the camera support of FIG. 13, and the camera clamp of FIG. 14, consistent with embodiments of the present disclosure;

FIG. 16 is another plan view of a camera mount including the base of FIG. 12, the camera support of FIG. 13, and the camera clamp of FIG. 14, consistent with embodiments of the present disclosure;

DETAILED DESCRIPTION

The present disclosure is generally directed to a digital optical video measurement system for comparing a manufactured part against a digital representation of the manufactured part or to a calibrated measurement standard related to the part. The measurement system may include one or more light sources for imparting light upon the manufactured part, a support for the manufactured part, and an optical video system for capturing images of the manufactured part. The measurement system may further include a display for presenting the captured digital images of the manufactured part and a digital representation (e.g., CAD file) of the manufactured part.

The optical video system includes a digital camera configured to capture one or more images of the manufactured part. The camera is configured to cooperate with one of several interchangeable lens assemblies for providing optics for the camera. The video measurement system further includes a mounting assembly configured to receive and retain a portion of an interchangeable lens assembly and to maintain alignment of the interchangeable lens assembly with the camera. The camera and mounting assembly may be configured to receive a variety of interchangeable lenses.

A digital video measurement system consistent with the present disclosure may allow a variety of interchangeable lenses (e.g., lenses of different magnifications) to be relatively quickly and easily coupled to and decoupled from the mounting assembly and digital camera as desired.

Figure 1:
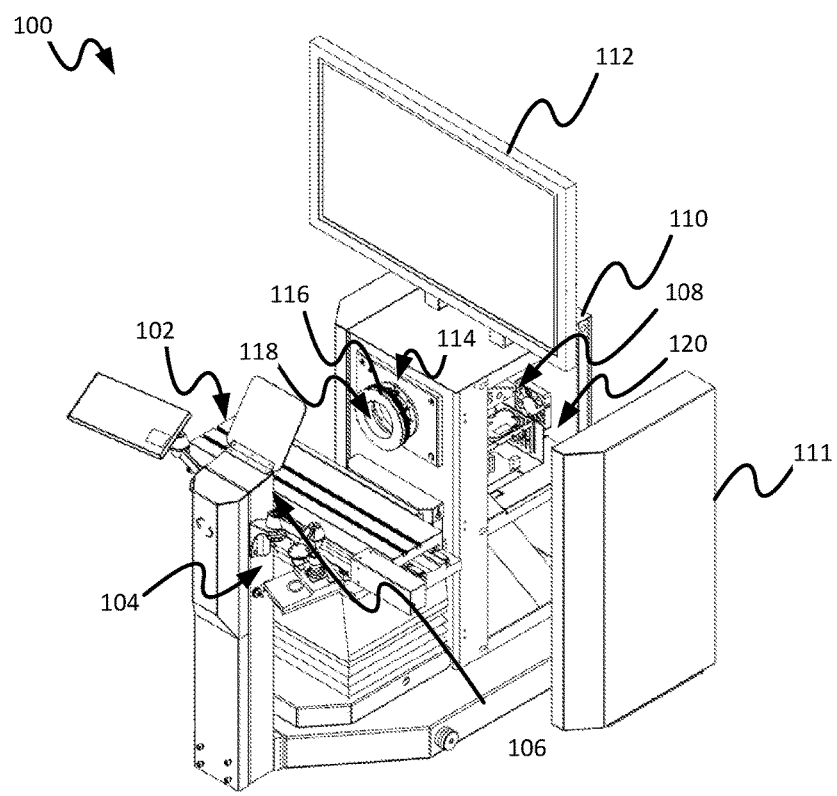
FIG. 1 is a perspective view of a digital video measurement system consistent with the present disclosure.

Turning to FIG. 1, a perspective view of a video measurement platform system 100 consistent with the present disclosure is illustrated. It should be noted that the video measurement platform system 100 illustrated in the figures of the present disclosure is one of many different embodiments of platform systems that may be included in a system consistent with the present disclosure. Accordingly, a variety of different configurations and mounting orientations may be included with a system described herein.

Generally, the measurement system 100 may include a stage 102 for supporting a manufactured part (not shown) thereon. The stage 102 may be multi-axis having three orthogonal axes X, Y, and Z of translation (i.e., linear motion). It should be noted that the stage 102 may include fewer axes of translation or one or more additional axes of rotation (i.e., angular motion). A variety of manual controls 104 may be associated with the stage 102 to adjust the position of the manufactured part. The manual controls 104 may include motors, actuators, or the like for automatically positioning and/or moving the manufactured part under inspection. In addition, at least the linear motion axes X and Y may be equipped with graduated linear encoders (not shown) for measuring the changes in the position of the manufactured part.

The measurement system 100 may further include at least one light source 106 configured to impart light upon and illuminate the manufactured part. The light source 106 may include, for example, light emitting diode (LED), incandescent, and arc lamps. The measurement system 100 may further include an optical video system 108 configured to capture one or more images and/or video of the manufactured part. As shown, the optical video system 108 may be enclosed within a housing 110 of the measurement system 100 and may be accessible via one or more removable panels 111 coupled to the housing 110. The captured images may be displayed on a monitor 112 upon which an operator may view the manufactured part.

The measurement system 100 may further include a data processing system (e.g., a computer) including a database of digital representations (e.g., CAD drawings) of manufactured parts. The data processing system may be configured to receive one or more images of the manufactured part and transmit the one or more images to the monitor 112 to be displayed. The data processing system may further be configured to transmit a corresponding CAD drawing or measurement information to the monitor 112. The CAD drawing may be digitally overlaid on the image of the manufactured part and a comparison of the manufactured part against the corresponding CAD drawing may be made. In addition to providing a visual display of the captured images of the manufactured part and a corresponding CAD drawing, the monitor 112 may provide a method for operator input. For example, in one embodiment, the monitor 112 may provide a touchscreen interface upon which an operator may interact with and manipulate the content (i.e., video images of the manufactured part and CAD drawing) being displayed. The touchscreen interface may further allow an operator to interact with (e.g., command input) software for measurement and comparison of the manufactured part with the corresponding CAD drawing.

As generally understood, the data processing system may include custom, proprietary, known, and/or after-developed surface and edge detection processing code (or instruction sets) that are generally well-defined and operable to measure the dimensions of the manufactured part and produce sub-pixel accurate measurements. The data processing system may further include custom, proprietary, known, and/or after-developed processing code (or instruction sets) that are generally well-defined and operable to import and overlay a corresponding CAD drawing with respect to the manufactured part and to compare dimensions (e.g., measurements and geometry) of the manufactured part against the corresponding CAD drawing. Commercially available software may be used for the measurement and/or comparison of the manufactured part against a corresponding CAD drawing overlay. For example, a data processing system consistent with the present disclosure may include M3 series performance metrology software for video and optical measuring systems offered by MetLogix (Manchester, N.H., USA).

The data processing system may include a storage medium configured to store captured images and/or video of the manufactured part. More specifically, the data processing system may be configured to store captured images and/or video of the manufactured part with or without the CAD drawing overlay, as well as corresponding measurements and data.

In the illustrated embodiment, the measurement system 100 may further include a mounting assembly 114 disposed on a portion of the housing 110. The mounting assembly 114 may be disposed proximate the stage 102. As shown, the mounting assembly 114 may include a flange member 116 defining a longitudinally disposed passageway 118. The passageway 118 may extend from an exterior of the housing 110 to an interior 120 of the housing 110. The passageway 118 may have a substantially cylindrical cross-section. As described in greater detail herein, the mounting assembly 114 may be configured to receive and retain a portion of the lens assembly.

Figure 2:
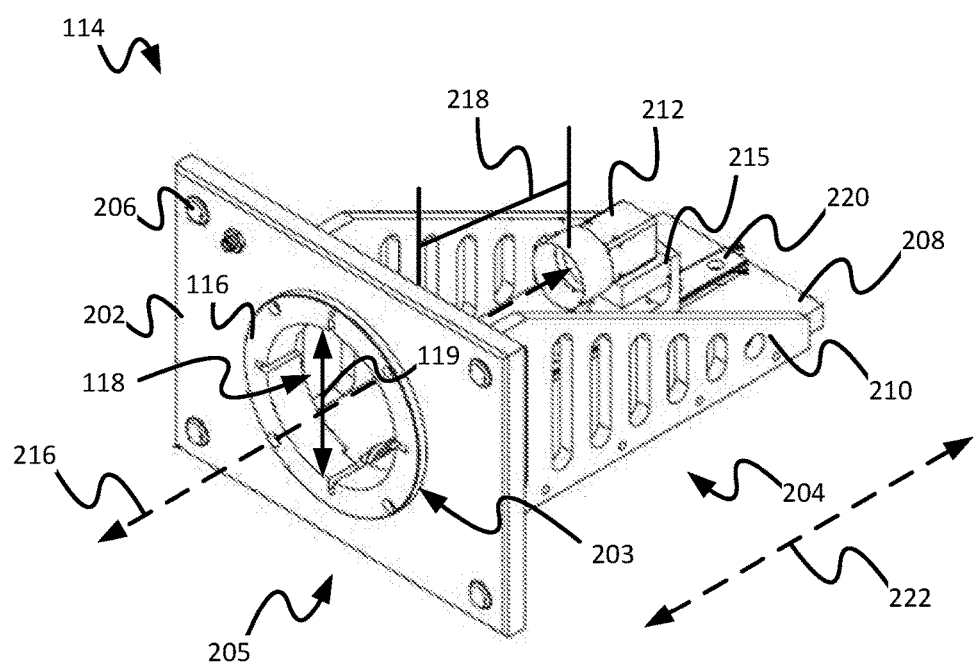
FIG. 2 is a perspective view of an example of a mounting assembly that may be used with the digital video measurement system of FIG. 1, consistent with embodiments of the present disclosure.

FIG. 2 shows a perspective view of an embodiment of the mounting assembly 114. As shown, the mounting assembly 114 includes a mounting plate 202 coupled to a carriage assembly 204 at a longitudinal end 205 of the mounting assembly 114. The mounting plate 202 may include a plurality of mounting fixtures 206 for coupling the mounting assembly 114 to the measurement system 100 of FIG. 1. The mounting fixtures 206 may include, for example, through holes for receiving a bolt and/or a screw. In some instances, the mounting fixtures 206 may include one or more openings that extend at least partially through and/or one or more protrusions that extend from the mounting plate 202, that are configured to form a snap-fit, a press-fit, and/or any other suitable form of coupling with a corresponding opening and/or protrusion. Additionally, or alternatively, in some instances, the mounting plate 202 may be coupled to the measurement system 100 by welding, adhesives, and/or any other suitable form of coupling.

The mounting plate 202 may be positioned at the longitudinal end 205 of the mounting assembly 114 and may include a flange opening 203 for receiving at least a portion of the flange member 116. Therefore, the flange opening 203 may be generally described as defining, at least in part, the passageway 118. Therefore, the flange member 116 may be coupled to the mounting plate 202 at the flange opening 203. In some instances, the flange member 116 may be integrally formed from the mounting plate 202 at the flange opening 203.

As shown, the carriage assembly 204 is coupled to and extends from the mounting plate 202. The carriage assembly 204 may include a platform 208, one or more support structures 210, and a camera 212. The mounting plate 202 may be coupled to the platform 208. The support structures 210 may be coupled to the mounting plate 202 and the platform 208. As shown, the support structures 210 may generally be described as forming a truss. However, the support structure 210 is not limited to such a configuration. For example, the support structure 210 may include one or more wires (or cables) extending from the mounting plate 202 to the platform 208. Therefore, the support structures 210 may be generally described as increasing the stability of the platform 208.

As also shown, the camera 212 may be coupled to the platform 208 using a camera mount 215. The camera mount 215 may be coupled to the platform 208 such that the camera 212 obtains a desired alignment relative to the passageway 118. For example, the camera mount 215 may position the camera 212 such that an optical axis 216 of the camera 212 aligns with a central axis of the passageway 118. The optical axis 216 may correspond to a central axis of one or more lenses included within the camera 212.

In some instances, the camera mount 215 is movably coupled to the platform 208 such that a separation distance 218 between the camera 212 and the mounting plate 202 can be adjusted. Therefore, when an interchangeable lens is received within the passageway 118, the platform 208 moves in response to the interchangeable lens engaging the camera 212. As such, a separation distance between various interchangeable lens assemblies and components positioned on the stage 102 of FIG. 1 may remain substantially constant, regardless of a length of the interchangeable lens assembly. In other words, the separation distance 218 may be increased and/or decreased to accommodate multiple lens assemblies of varying length, as will be discussed further herein.

In some instances, the camera mount 215 may be slideably coupled to a track 220 that extends longitudinally along the platform 208 such that the camera mount 215 may be movable along a longitudinal axis 222 of the mounting assembly 114. Therefore, the track 220 may generally be described as being coupled to the platform 208 such that the track 220 extends longitudinally between two ends of the platform 208. In these instances, when a lens assembly is positioned within the flange member 116 the lens assembly may engage the camera 212 such that the camera mount 215 slides longitudinally along the track 220. In some instances, a biasing mechanism may urge the camera mount 215 along the track 220 towards the mounting plate 202 such that a consistent (e.g., uniform and/or desired) engagement between the camera 212 and a respective lens assembly can be obtained, regardless of a length of the lens assembly, as will be discussed further herein.

The camera 212 may include any digital camera capable of capturing digital images. Therefore, the camera 212 may include a video camera (e.g., camera configured to capture moving images comprised of a plurality of frames). In some instances, the camera 212 may be capable of capturing hi-resolution images in real-time (i.e., at or near the camera's full frame rate) for a live video image of the manufactured part. Additionally, or alternatively, the camera 212 may include a still camera (e.g., camera configured to capture still photographs). The camera 212 may be configured to operate using light in the visible spectrum or with other portions of the electromagnetic spectrum, for example, the infrared spectrum, ultraviolet spectrum, and/or any other suitable spectrum.

Figure 3:
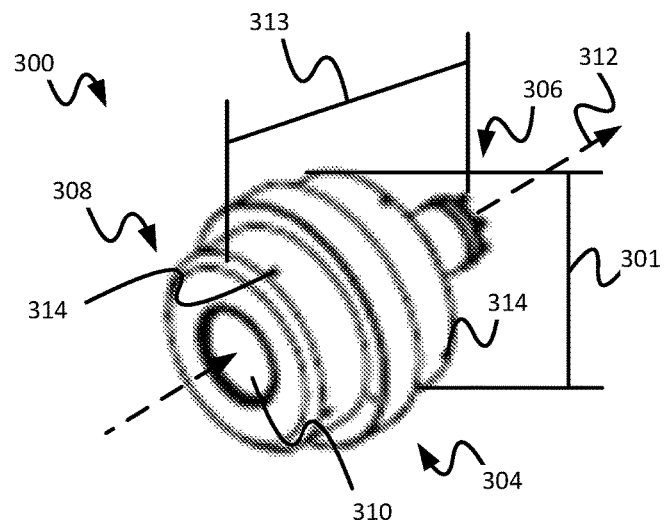
FIG. 3 is a perspective view of an example of an interchangeable lens assembly that may be used with the digital video measurement system of FIG. 1, consistent with embodiments of the present disclosure.
Figure 4:
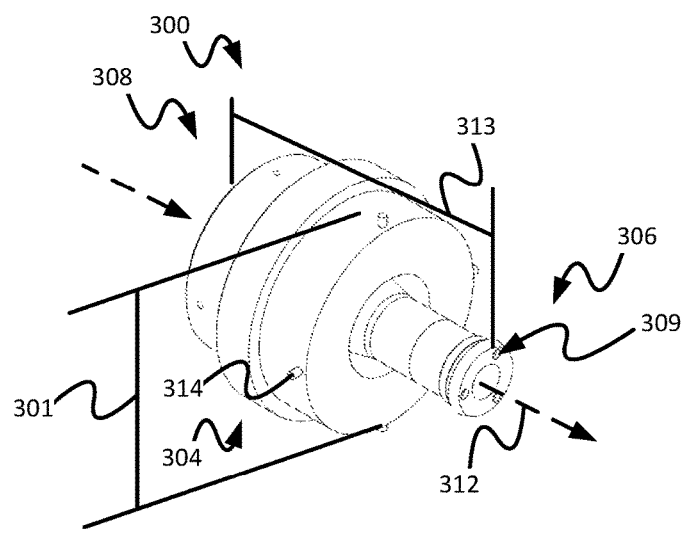
FIG. 4 is another perspective view of the interchangeable lens assembly of FIG. 3, consistent with embodiments of the present disclosure.
Figure 5:
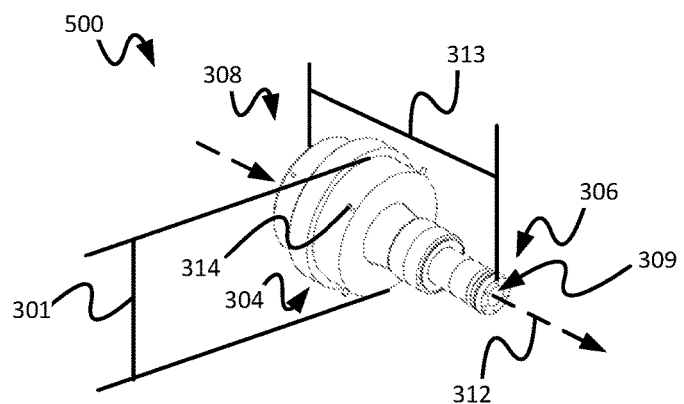
FIG. 5 is a perspective view of another example of an interchangeable lens assembly that may be used with the digital video measurement system of FIG. 1, consistent with embodiments of the present disclosure.
Figure 6:
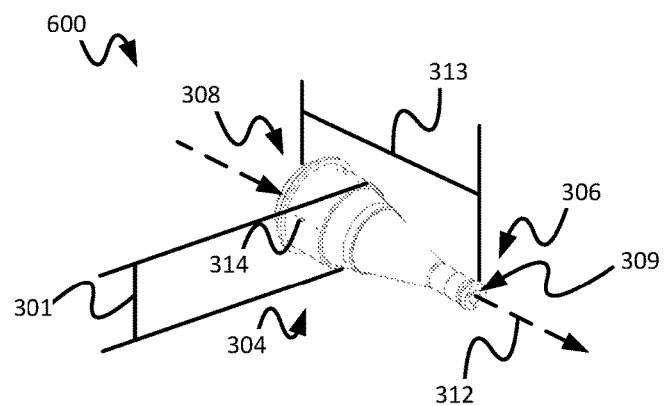
FIG. 6 is a perspective view of another example of an interchangeable lens assembly that may be used with the digital video measurement system of FIG. 1, consistent with embodiments of the present disclosure.

FIGS. 3 to 4 show perspective views of an embodiment of an interchangeable lens assembly 300 and FIGS. 5 to 6 show perspective views of embodiments of interchangeable lens assemblies 500 and 600, each of the interchangeable lens assemblies 300, 500, and 600 being capable of being received within the passageway 118 of the mounting assembly 114 of the measurement system 100 of FIG. 1. Therefore, a diameter 119 (FIG. 2) of the passageway 118 may generally correspond to a width 301 of each of the interchangeable lens assemblies 300, 500, and 600. In some instances, at least a portion of each of the lens assemblies 300, 500, and 600 may slideably engage at least a portion of the passageway 118. Therefore, in some instances, the width 301 may be constant between each of the interchangeable lens assemblies 300, 500, and 600.

As shown, the interchangeable lens assemblies 300, 500, and 600 include a body 304 having a proximal end 306 and a distal end 308. A cavity 309 extends between the proximal end 306 and the distal end 308 such that light received by a lens 310 at the distal end 308 passes along a light path 312 extending through the cavity 309 and out the proximal end 306. The lens 310 may magnify an object positioned within the field of view (or angle of view) of the lens 310. In some instances, the lens 310 may include telecentric properties. In other words, the lens 310 may be a telecentric lens.

The properties of the lens 310 (e.g., the extent of the magnification and/or the field view) may vary between each of the interchangeable lens assemblies 300, 500, and 600. For example, an operator of the measurement system 100 may select a respective interchangeable lens assembly 300, 500, and 600 to achieve a desired functionality of the measurement system 100. Therefore, in some instances, the physical dimensions may vary between the interchangeable lens assemblies 300, 500, and 600. For example, an assembly length 313 may change between each of the interchangeable lens assemblies 300, 500, and 600.

As also shown, the interchangeable lens assemblies 300, 500, and 600 may include one or more protrusions 314 extending from the body 304. The one or more protrusions 314 may be, for example, used in coupling the lens assemblies 300, 500, and 600 to the measurement system 100. For example, the protrusions 314 may form a portion of a bayonet coupling, as discussed further herein. However, the lens assemblies 300, 500, and 600 are not limited to being coupled to the measurement system 100 using a bayonet coupling. For example, the lens assemblies 300, 500, and 600 may be coupled to the measurement system 100 using one or more of a threaded coupling, a friction fit coupling, a magnetic coupling, one or more latches, and/or any other suitable form of coupling.

While the interchangeable lens assemblies 300, 500, and 600 have been discussed collectively herein, each of the interchangeable lens assemblies 300, 500, and 600 may have different geometries and/or features such that an operator of the measurement system 100 is able to interchange lens assemblies to obtain a desired functionality. In other words, the interchangeable lens assemblies 300, 500, and 600 are interchangeable to provide different functionality to the measurement system 100 (e.g., a degree magnification).

For example, the lens 310 included in the lens assembly 300 may be a bi-telecentric lens having a 0.243× magnification, the lens 310 included in the lens assembly 500 may include a bi-telecentric lens having 0.157× magnification, and the lens 310 included in the lens assembly 600 may include a bi-telecentric lens having a 0.110× magnification.

Figure 7:
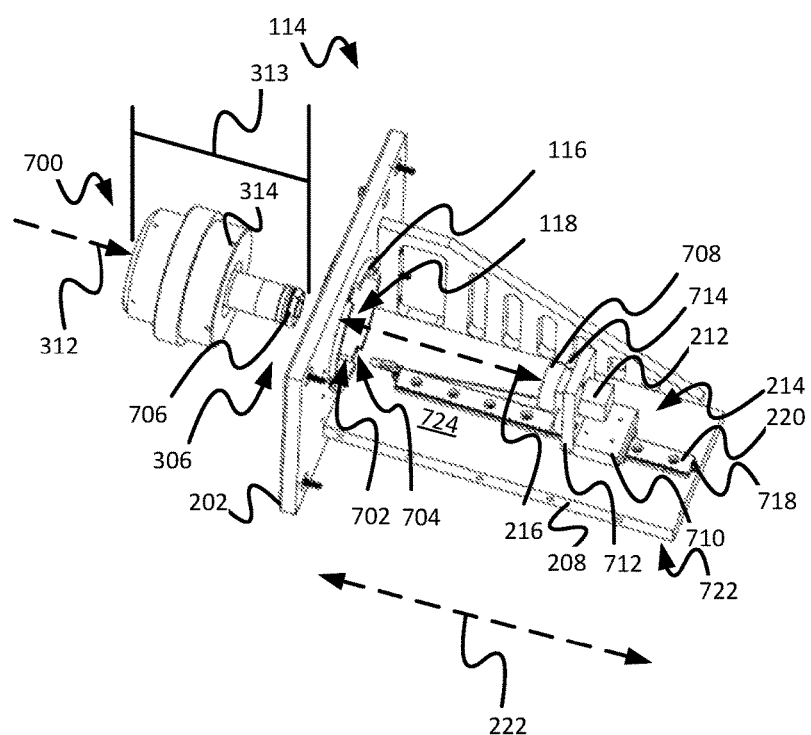
FIG. 7 is a perspective view of an example of the mounting assembly of FIG. 2, consistent with embodiments of the present disclosure.

FIG. 7 shows a perspective view of an embodiment of the mounting assembly 114 receiving an interchangeable lens assembly 700 which may be an example of any one of the interchangeable lens assemblies 300, 500, and 600. At least a portion of the interchangeable lens assembly 700 is received within the passageway 118 when the interchangeable lens assembly 700 is coupled to the flange member 116. As shown, the flange member 116 includes one or more longitudinal grooves 702 for receiving a corresponding protrusion 314 extending parallel to (or along) the longitudinal axis 222. Each of the longitudinal grooves 702 may extend (or transition) into a transverse slot 704 that is transverse to the longitudinal axis 222. When the interchangeable lens assembly 700 is fully seated in the flange member 116 (e.g., further movement in the direction of the camera 212 is prevented by the contact between the interchangeable lens assembly 700 and the flange member 116), the interchangeable lens assembly 700 may be coupled to the flange member 116 by rotating the interchangeable lens assembly 700 such that the protrusions 314 engage a corresponding transverse slot 704. In other words, each of the protrusions 314 forms a bayonet coupling with a corresponding longitudinal groove 702 and transverse slot 704. Therefore, the longitudinal groove 702 and the transverse slot 704 may generally be described as collectively defining a portion of a bayonet coupling. Once the interchangeable lens assembly 700 is coupled to the flange member 116, a biasing mechanism, as discussed herein, may urge each of the protrusions 314 into engagement (e.g., contact) with at least a portion of the transverse slot 704.

When the interchangeable lens assembly 700 is coupled to the flange member 116 the light path 312 may align with the optical axis 216 of the camera 212. Therefore, the proximal end 306 of the interchangeable lens assembly 700 may engage the camera 212 such that light exiting the proximal end 306 of the interchangeable lens assembly 700 is received by the camera 212. To facilitate this engagement, the proximal end 306 of the interchangeable lens assembly 700 may include a fitting (or sleeve) 706 capable of being at least partially received within a receptacle 708 (e.g., a C-mount) coupled to the camera 212. In other words, the interchangeable lens assembly 700 may generally be described as engaging the receptacle 708 of the camera 212.

The fitting 706 may include a resilient and durable material capable of elastic expansion when a force is applied thereto and elastic recovery when the force is removed therefrom. The material may include, for example, either natural or synthetic materials such as polymers and/or co-polymers. Examples may include polyurethane, latex, natural rubber, nylon (polyamides), polyester, polyethylene, polypropylene, PVC, fluoroplastics, block copolymers, polyethers and composites thereof.

Figure 8:
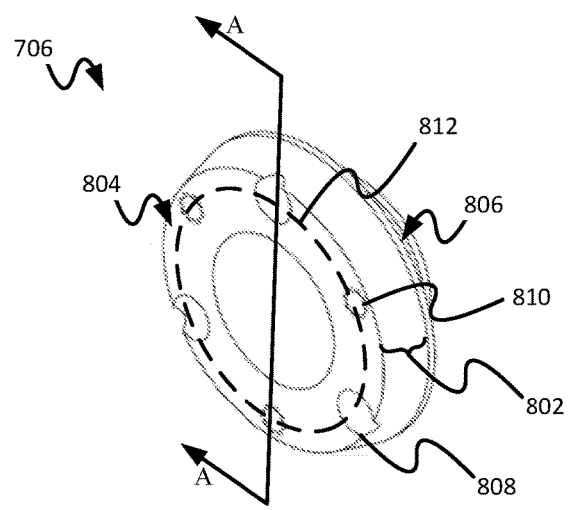
FIG. 8 is a perspective view of an example of a fitting for an interchangeable lens assembly such as one or more of the interchangeable lens assemblies of FIGS. 3-6, consistent with embodiments of the present disclosure.

FIG. 8 shows a perspective view of an example of the fitting 706. The fitting 706 may include a fitting tapered region 802 that tapers from a camera facing surface 804 towards a lens assembly facing surface 806. The fitting tapered region 802 may be generally described as facilitating the engagement between the interchangeable lens assembly 700 of FIG. 7 with the receptacle 708 of FIG. 7. In other words, the fitting tapered region 802 may at least partially align the fitting 706 with the receptacle 708.

The fitting 706 may also include a first set of openings 808 and a second set of openings 810. The first and/or second sets of openings 808 and 810 may extend from the camera facing surface 804 to the lens assembly facing surface 806. Therefore, the first and/or second sets of openings 808 and 810 may be used, for example, when coupling the fitting 706 to the interchangeable lens assembly 700. As shown, the first and second sets of openings 808 and 810 may be equally spaced along a common circular axis 812.

Figure 9:
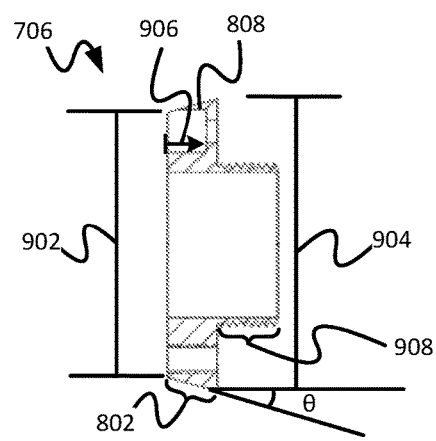
FIG. 9 is a cross-sectional view of the fitting of FIG. 8 taken along the line A-A, consistent with embodiments of the present disclosure.

FIG. 9 shows a cross-sectional view of the fitting 706 taken along the line A-A of FIG. 8. As shown, the fitting tapered region 802 tapers from a camera facing surface width 902 to a lens assembly facing surface width 904. The camera facing surface width 902 and the lens assembly facing surface width 904 may be such that the fitting tapered region 802 has a fitting taper angle θ. The fitting taper angle θ may measure, for example, in a range of 10° and 20°. More specifically, for example, the fitting taper angle θ may measure 15°. By way of further example, the camera facing surface width 902 may measure in a range of 2 centimeters (cm) to 5 cm and the lens assembly facing surface width 904 may measure in a range of 3 cm to 6 cm. Even more specifically, for example, the camera facing surface width 902 may measure 3.78 cm and the lens assembly facing surface width 904 may measure 4.11 cm.

As shown, the first set of openings 808 may be counter sunk by a counter sunk depth 906. The counter sunk depth 906 may, for example, measure in a range of 0.25 cm to 1.5 cm. More specifically, for example, the counter sunk depth 906 may measure 0.56 cm.

As also shown, the fitting 706 may include a threaded region 908 capable of threadably engaging a corresponding threaded region of the interchangeable lens assembly 700. The threaded region 908 extends from the lens assembly facing surface 806 such that the threaded region 908 can be received within a threaded opening of the interchangeable lens assembly 700. Therefore, the fitting 706 may be generally described as being threadably coupled to the interchangeable lens assembly 700. Additionally, or alternatively, the fitting 706 may be coupled to the interchangeable lens assembly 700 using one or more of an adhesive, a snap-fit, a press-fit, a bolt or screw, and/or any other suitable form of coupling.

Figure 10:
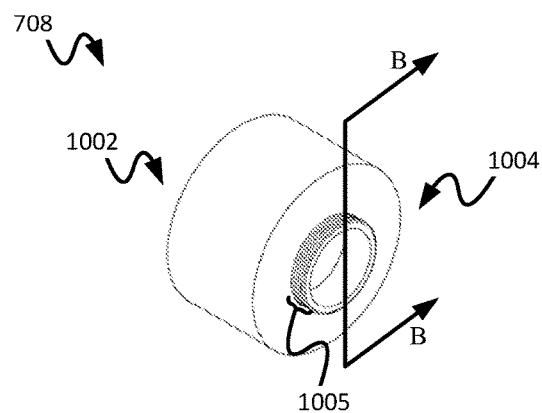
FIG. 10 is a perspective view of a receptacle for a camera that may be coupled to the mounting assembly of FIG. 7, consistent with embodiments of the present disclosure.

FIG. 10 shows a perspective view of the receptacle 708 of FIG. 7. As shown, the receptacle 708 has a lens assembly receiving end 1002 and a camera receiving end 1004. The camera receiving end 1004 may include a threaded region 1005 for threadably coupling the receptacle 708 to the camera 212 of FIG. 7. Additionally, or alternatively, the receptacle 708 may be coupled to the camera 212 using one or more of an adhesive, a snap-fit, a press-fit, a bolt or screw, and/or any other suitable form of coupling.

Figure 11:
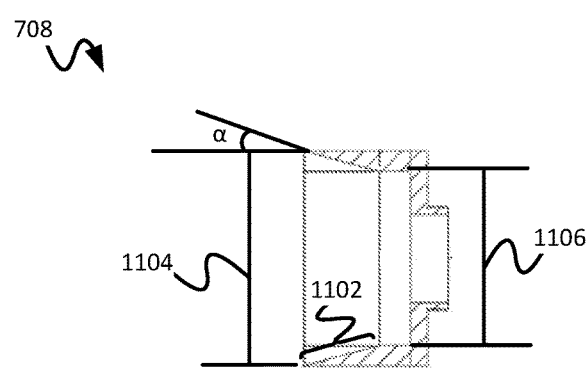
FIG. 11 is a cross-sectional view of the receptacle of FIG. 10 taken along the line B-B, consistent with embodiments of the present disclosure.

FIG. 11 shows a cross-sectional view of the receptacle 708 of FIG. 10 taken along the line B-B. As shown, the receptacle 708 includes a receptacle tapered region 1102. The receptacle tapered region 1102 generally corresponds to the fitting tapered region 802 of FIG. 8. Therefore, the receptacle tapered region 1102 may taper from an opening width 1104 to a first interior width 1106. The opening width 1104 may generally correspond to the lens assembly facing surface width 904 and the first interior width 1106 may generally correspond to the camera facing surface width 902 of the fitting 706 of FIG. 9. Therefore, the receptacle tapered region 1102 may have a receptacle taper angle α that corresponds to the fitting taper angle θ. As such, the receptacle tapered region 1102 and the fitting tapered region 802 may generally be described as interacting to align the optical axis 216 of the camera 212 with the light path 312 extending through the interchangeable lens assembly 700.

The opening width 1104 may measure, for example, in a range of 3 cm to 6 cm and the first interior width 1106 may measure, for example, in a range of 2 cm to 5 cm. Even more specifically, the opening width 1104 may measure, for example, 5.03 cm and the first interior width 1106 may measure, for example, 4.11 cm.

Referring again to FIG. 7, the camera 212 is coupled to a camera mount 214 which may be an embodiment of the camera mount 215 of FIG. 2 such that the optical axis 216 of the camera 212 is aligned with the light path 312. As shown, the camera mount 212 includes a camera mount base 710, a camera support 712 coupled to the camera mount base 710, and a camera clamp 714 coupled to the camera mount support 712. The camera mount base 710 slideably engages the track 220 such that the receptacle 708 is capable of maintaining a consistent (e.g., uniform and/or desired) engagement (e.g., contact) with the fitting 706. In other words, a position of the camera mount base 710 relative to the track 220 may be adjustable to obtain a desired engagement between the receptacle 708 coupled to the camera 212 and the fitting 706 coupled to the interchangeable lens assembly 700.

The camera support 712 extends from and is coupled to the camera mount base 710. The camera support 712 receives at least a portion of the camera 212 such that the optical axis 216 of the camera 212 is capable of being aligned with the light path 312 of the interchangeable lens assembly 700. In some instances, when the camera 212 is received by the camera support 712, the optical axis 216 of the camera 212 is aligned with the light path 312 of the interchangeable lens assembly 700.

The camera clamp 714 receives at least a portion of the camera 212 such that the camera clamp 714 is capable of engaging at least a portion of the camera 212 (e.g., the receptacle 708). The camera clamp 714 may be adjustable such that an engagement force applied by the camera clamp 714 to the camera 212 is adjustable. Therefore, in some instances, the engagement force may be adjusted such that the camera 212 is rotatable relative to the camera clamp 714 such that a desired rotational alignment can be obtained. When a desired rotational alignment of the camera 212 is obtained, the engagement force of the camera clamp 714 may be adjusted such that the camera 212 is not rotatable relative to the camera clamp 714. In some instances, the desired rotational alignment may be based, at least in part, on the orientation of the camera 212 relative to, for example, the stage 102 of FIG. 1. For example, the camera 212 may be rotated such that a surface of the camera 212 is parallel with, for example, the stage 102. In other words, the rotation of the camera 212 relative to the camera clamp 714 may be for the purpose of leveling the camera 212. Further, in some instances, the engagement between the camera clamp 714 and the camera 212 may at least partially align the optical axis 216 of the camera 212 with the light path 312 of the interchangeable lens assembly 700.

Figure 12:
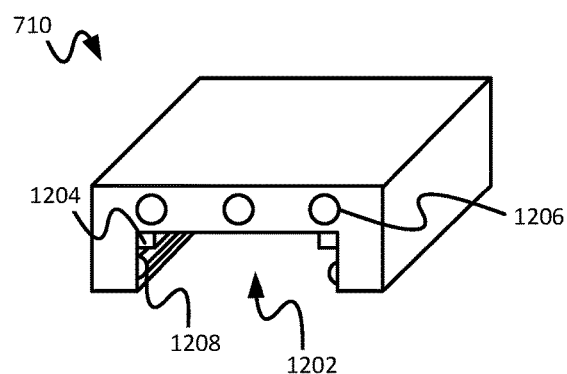
FIG. 12 is a schematic perspective view of a base for a camera mount, consistent with embodiments of the present disclosure.

FIG. 12 shows a schematic perspective view of an embodiment of the camera mount base 710. The camera mount base 710 may include a groove 1202 extending through the camera mount base 710. The groove 1202 may slideably engage the track 220 of FIG. 7. The groove 1202 may include (and/or be coupled to) one or more bearings 1204 (e.g., slide bearings, ball bearings, roller bearings, and/or any other suitable bearing). In some instances, the one or more bearings 1204 may be coupled to the camera mount base 710 using, for example, one or more of a bolt, a screw, a press-fit, a snap fit, an adhesive, and/or any other suitable form of coupling. The bearings 1204 may engage the track 220 such that the camera mount base 710 moves relative to the track 220. In some instances, the groove 1202 may include one or more protrusions 1208 for engaging a corresponding recess of the track 220 such that the base 710 may be prevented from disengaging the track 220.

As shown, the camera mount base 710 may include one or more camera support mounts 1206 for coupling the camera support 712 of FIG. 7 to the camera mount base 710. The camera support mounts 1206 may be a threaded opening such that, for example, the camera support 712 can be coupled to the camera mount base 710 using one or more bolts or screws. In some instances, the camera support mounts 1206 may be one or more openings and/or protrusions capable of forming a press-fit and/or snap-fit with a corresponding one or more opening and/or protrusions of the camera support 712.

Figure 13:
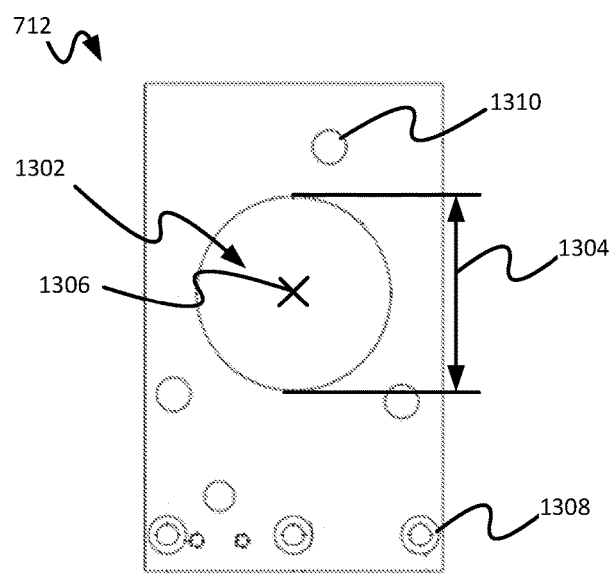
FIG. 13 is a plan view of a camera support capable of being coupled to the base of FIG. 12, consistent with embodiments of the present disclosure.

FIG. 13 shows a plan view of an embodiment of the camera support 712 of FIG. 7. The camera support 712 may include a camera opening 1302 defining a passageway through the camera support 712 for receiving at least a portion of the camera 212. Therefore, a diameter 1304 of the camera opening 1302 may be based, at least in part, on a width of the camera 212 of FIG. 7 (e.g., a width of the receptacle 708 of FIG. 7).

A central axis 1306 of the passageway defined by the camera opening 1302 may be aligned with the light path 312 of the interchangeable lens assembly 700 of FIG. 7 such that, when the camera 212 is positioned within the camera opening 1302, the optical axis 216 of the camera 212 is capable of being aligned with the light path 312. In other words, the optical axis 216 of the camera 212 may be aligned with the central axis 1306 of the passageway defined by the camera opening 1302 when the camera 212 is positioned within the camera opening 1302.

The camera support 712 may be coupled to the camera mount base 710 using the camera mount base mounts 1308. The camera mount base mounts 1308 may include an opening capable of receiving a threaded fastener such that, for example, the camera mount base 710 can be coupled to the camera support 712 using one or more bolts or screws. In some instances, the camera mount base mounts 1308 may be one or more openings and/or protrusions capable of forming a press-fit and/or snap-fit with a corresponding one or more openings and/or protrusions of the camera mount base 710.

The camera support 712 may also include one or more clamp mounts 1310 for coupling the camera clamp 714 of FIG. 7 to the camera support 712. The clamp mounts 1310 may be a threaded opening such that, for example, the camera clamp 714 can be coupled to the camera support 712 using one or more bolts and/or screws. In some instances, the clamp mounts 1310 may be one or more openings and/or protrusions capable of forming a press-fit and/or snap-fit with a corresponding one or more openings and/or protrusions of the camera clamp 714.

FIG. 14 shows a plan view of an embodiment of the camera clamp 714 of FIG. 7. The camera clamp 714 may include an irregular shaped opening 1402 that defines a passageway that extends through the camera clamp 714. The irregular shaped opening 1402 may include one or more raised regions 1404 and recessed regions 1406. The one or more raised regions 1404 engage at least a portion of the camera 212 of FIG. 7 (e.g., the receptacle 708). A central axis 1405 of the passageway defined by the irregular shaped opening 1402 may align with the light path 312 of the interchangeable lens assembly 700 of FIG. 7 such that when the camera 212 is positioned within the irregular shaped opening 1402 the optical axis 216 of the camera 212 is capable of being aligned with the light path 312. In other words, the optical axis 216 of the camera 212 may be aligned with the central axis 1405 of the passageway defined by the irregular shaped opening 1402.

The camera clamp 714 may also include a separation gap 1408 that is capable of being opened or closed in response to a threaded fastener engaging a clamping opening 1410 (shown in hidden lines in FIG. 14). The clamping opening 1410 extends from a first portion 1412 of the camera clamp 714 to a second portion 1414 of the camera clamp 714, wherein at least a portion of the first portion 1412 is opposite at least a portion of the second portion 1414 across the separation gap 1408. As a thread fastener is rotated within the clamping opening 1410, a separation gap width 1416 increases or decreases such that the engagement force applied by the camera clamp 714 on the camera 212 decreases or increases, respectively. Prior to the insertion of a threaded fastener into the clamping opening 1410, the separation gap width 1416 may measure, for example, in a range of 0.1 cm to 0.3 cm. More specifically, for example, the separation gap width 1416 may measure 0.2 cm.

The camera clamp 714 may also include one or more support mounts 1418 capable of coupling the camera clamp 714 to the camera support 712. As shown, the support mounts 1418 are positioned on the camera clamp 714 such that at least a portion of the camera clamp 714 is movable relative to the camera support 712 in response to the rotational movement of a threaded fastener within the clamping opening 1410. The support mounts 1418 may include an opening capable of receiving a threaded fastener such that, for example, the camera support 712 can be coupled to the camera clamp 714 using one or more bolts or screws. In some instances, the support mounts 1418 may be one or more openings and/or protrusions capable of forming a press-fit and/or snap-fit with a corresponding one or more openings and/or protrusions of the camera support 712.

While the irregular shaped opening 1402 is generally shown and described as having an irregular shape, such a configuration is not required. For example, the irregular shaped opening 1402 may be substantially circular.

FIGS. 15 and 16 show an assembled example of an embodiment the camera mount 214 with various openings and/or passageways illustrated as hidden lines (e.g., the groove 1202, the camera support mounts 1206, the camera mount base mounts 1308, the clamp mounts 1310, the clamping opening 1410, and/or the support mounts 1418). As shown, the camera support 712 is coupled to the camera mount base 710 such that the camera support 712 does not extend into the groove 1202. However, in some instances, the camera support 712 may include a cutout that generally corresponds to the groove 1202. As also shown, a foot print (e.g., the length and width of the camera clamp 714) of the camera clamp 714 may be less than a footprint of the camera support 712 (e.g., the length and width of the camera support 712). However, in some embodiments, the footprint of the camera clamp 714 may be substantially equal to the footprint of the camera support 712. While the camera mount base 710, the camera support 712, and the camera clamp 714 are generally described as being coupled together using mechanical couplers (e.g., one or more of, bolts/screws, press-fits, snap fits, and the like), the camera mount base 710, the camera support 712, and the camera clamp 714 may be additionally, or alternatively, coupled together using any one or more of adhesives, welding, and/or any other suitable form of coupling.

Figure 17:
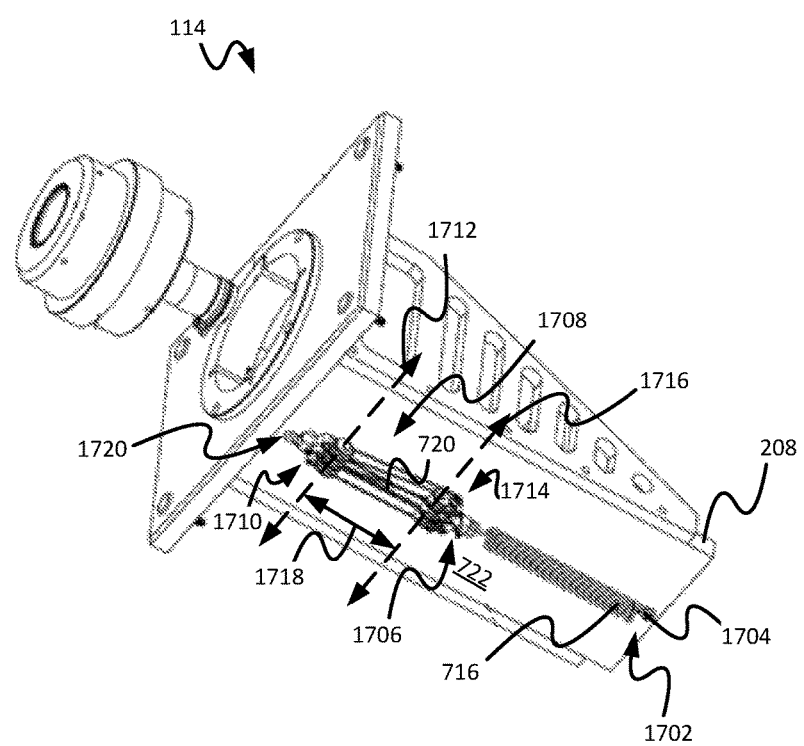
FIG. 17 is a perspective view of the mounting assembly of FIG. 7 having a biasing mechanism coupled thereto, consistent with embodiments of the present disclosure.

Referring again to FIG. 7 and also to FIG. 17, wherein FIG. 17 shows a perspective view of an example of the mounting assembly 114 having a biasing mechanism 716 and a pulley system 1708 coupled to a bottom surface 722 of the platform 208.

The biasing mechanism 716 may urge the receptacle 708 of the camera 212 into engagement with the fitting 706 of the interchangeable lens assembly 700. Therefore, the biasing mechanism 716 may urge the camera mount 214 along the track 220 in a direction of the mounting plate 202. As such, the biasing mechanism 716 may generally be described as urging the camera mount 214 in a direction of the interchangeable lens assembly 700 in order to maintain a desired (e.g., uniform, constant, and/or consistent) engagement (e.g., contact) between the receptacle 708 of the camera 212 and the fitting 706 of the interchangeable lens assembly 700. As such, multiple interchangeable lens assemblies (e.g., lens assembly 300, 500, and/or 600), each having a having a different assembly length 313, may be received within the passageway 118 while still maintaining a desired (e.g., uniform, constant, and/or consistent) engagement between the interchangeable lens assembly 700 and the receptacle 708. Further, the biasing mechanism 716 may urge the one or more protrusions 314 of the interchangeable lens assembly 700 into contact with respective transverse slots 704 (FIG. 7) of the flange member 116 when the interchangeable lens assembly 700 is coupled to the flange member 116.

When the interchangeable lens assembly 700 is inserted into the passageway 118, the interchangeable lens assembly 700 engages the camera 212 such that the camera mount 214 moves in a direction along the track 220 away from the mounting plate 202. However, when the interchangeable lens assembly 700 is removed from the passageway 118, the biasing mechanism 716 urges the camera mount 214 along the track in a direction of the mounting plate 202. To prevent the camera mount 214 from coming out of engagement with the track 220 one or more stops 718 may be positioned at distal ends of the track 220. In some instances, the positions of the stops 718 may be adjustable such that the stops 718 may be positioned at locations between the distal ends of the track 220.

The biasing mechanism 716 may include one or more of, for example, a spring (e.g., a compression spring, a tension spring, a torsional spring, and/or any other suitable spring), one or more elastic belts capable of elastic deformation, and/or any other suitable biasing mechanism. As shown, in some instances, at least a portion of the biasing mechanism 716 may be positioned on a bottom surface 722 of the platform 208 and the track 220 may be coupled to a top surface 724 of the platform 208, wherein the bottom surface 722 is opposite the top surface 724. In other words, at least a portion of the biasing mechanism 716 and the track 220 may be positioned on opposite sides of the platform 208. The use of the terms "bottom" and "top" in relation to surfaces 722 and 724 is for the purposes of clarity only and not limitation.

Referring to FIG. 17, a first end 1702 of the biasing mechanism 716 may be coupled to the platform 208 at a coupling point 1704. A second end 1706 of the biasing mechanism 716 may be coupled to the pulley system 1708 such that the second end 1706 is movable relative to the platform 208. The pulley system 1708 may include a fixed set of pulleys 1710 aligned along a first pulley axis 1712 and a suspended set of pulleys 1714 aligned along a second pulley axis 1716. The first and second pulley axes 1712 and 1716 may be parallel and separated from each other by a separation distance 1718.

The fixed set of pulleys 1710 may be coupled to the bottom surface 722 of the platform 208 such that the fixed set of pulleys 1710 are fixed relative to the platform 208. The suspended set of pulleys 1714 may be moveable relative to the bottom surface 722 of the platform 208. For example, the suspended set of pulleys 1714 may be suspended between the coupling point 1704 and the fixed set of pulleys 1710 such that a block-and-tackle type system is formed. The suspended set of pulleys 1714 may be suspended by a cable 720 extending around one or more pulleys included in the fixed set of pulleys and the suspended set of pulleys 1714.

The cable 720 may be a fiber cable. One example of a fiber cable, which may be used as the cable 720, may be a cable comprising Spectra® fiber, which is a registered trademark of Honeywell International, headquartered in Morris Plains, N.J.

Figure 18:
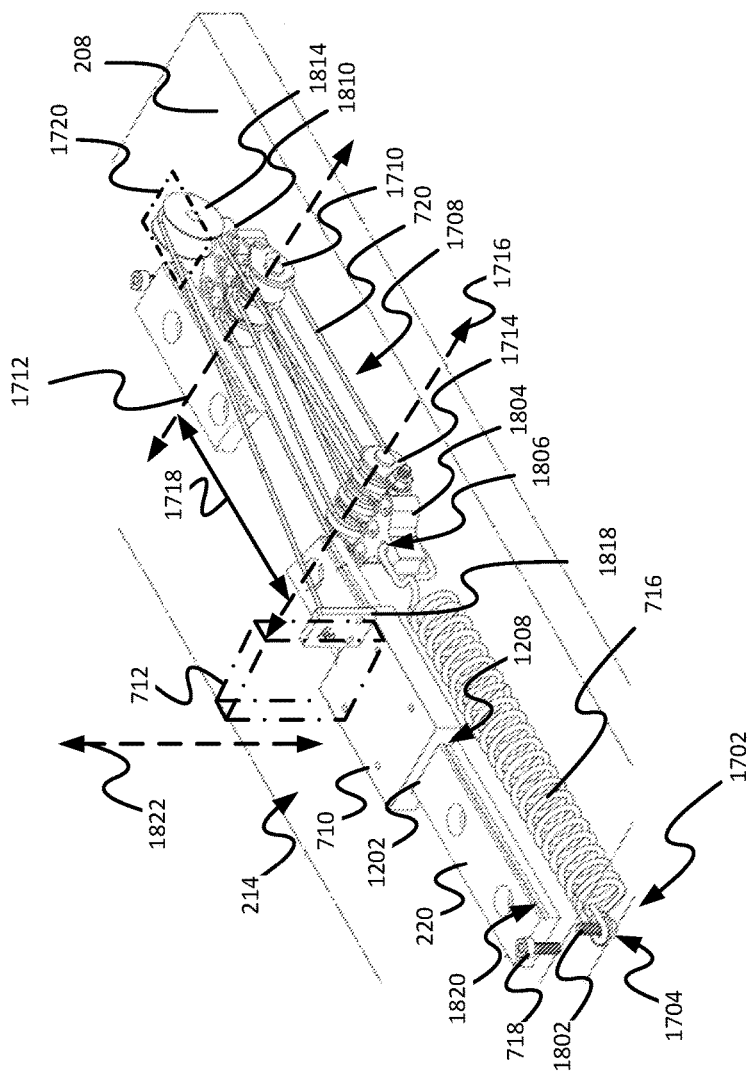
FIG. 18 is a transparent perspective view of a platform for the mounting assembly of FIG. 7 showing the biasing mechanism coupled thereto, consistent with embodiments of the present disclosure.

FIG. 18 shows a perspective view of the biasing mechanism 716 and the pulley system 1708 of FIG. 17 coupled to the platform 208, wherein the platform 208 is shown as transparent for the purposes of illustration. As shown, the first end 1702 of the biasing mechanism 716 is coupled to the platform 208 at the coupling point 1704 using a protruding member 1802. As shown, the protruding member 1802 may be a threaded fastener, such as a bolt or a screw. However, the protruding member 1802 is not limited to being a bolt or a screw. For example, the protruding member 1802 may be a shaft or a rod extending from the platform 208 and may be integrally formed from or coupled to the platform 208. For example, the protruding member 1802 may be coupled to the platform 208 at an opening extending at least partially through the platform 208 using one or more of a press-fit, a snap-fit, an adhesive, and/or any other suitable form of coupling.

The biasing mechanism 716 may extend from the coupling point 1704 to the pulley system 1708. The pulley system 1708 may be generally described as including a suspended pulley block 1804 including and/or coupled to the suspended set of pulleys 1714, a fixed pulley block 1810 including and/or coupled to the fixed set of pulleys 1710, and an additional pulley 1814 coupled within a passageway defined by the cable opening 1720.

As shown, the biasing mechanism 716 may be a tension spring extending from the coupling point 1704 to the suspended pulley block 1804. The suspended pulley block 1804 may include a pulley block opening 1806 that defines a passageway extending through the suspended pulley block 1804. The pulley block opening 1806 receives at least a portion of the biasing mechanism 716 such that the biasing mechanism 716 is coupled to the suspended pulley block 1804 at the pulley block opening 1806. Therefore, the second end of the biasing mechanism 716 may generally be described as being coupled to the suspended set of pulleys 1714.

The suspended pulley block 1804 and the suspended set of pulleys 1714 move relative to the platform 208 in response to a tensile force applied to the cable 720. The movement of the suspended pulley block 1804 causes the biasing mechanism 716 to extend/contract such that the separation distance 1718 between the first and second pulley axes 1712 and 1716 decreases/increases, respectively. As the separation distance 1718 decreases, a length of the cable 720 extending from the cable opening 1720 to the camera mount 214 increases. In other words, as the separation distance 218 between the camera 212 and the mounting plate 202 of FIG. 2 increases, the separation distance 1718 between the first and second pulley axes 1712 and 1716 decreases.

The fixed pulley block 1810 may be coupled to the platform 208 such that the fixed pulley block 1810 does not move relative to the platform 208 in response to the application of a tensile force to the cable 720. Therefore, the fixed set of pulleys 1710 may be generally described as being coupled to the bottom surface 722 of the platform 208. As shown, the fixed pulley block 1810 may be positioned proximate the cable opening 1720. The additional pulley 1814 may be rotatably coupled to one or more sidewalls of the passageway defined by the cable opening 1720 such that the additional pulley 1814 is capable of rotation relative to the cable opening 1720.

The cable 720 may extend around each pulley of the fixed set of pulleys 1710 and the suspended set of pulleys 1714. One end of the cable 720 may pass through the cable opening 1720 extend around the additional pulley 1814 within the cable opening 1720, and couple to the camera mount 214. Another end of the cable 720 may be coupled to a location proximate to or on the pulley system 1708 (e.g., the cable 720 may be coupled to the platform 208, the suspended pulley block 1804, or any other suitable location) such that the cable 720 does not come out of engagement with each the pulleys included within the fixed and suspended sets of pulleys 1710 and 1714 in response to a tensile force applied to the cable 720. In other words, the cable 720 may extend around each of the pulleys of the fixed and suspended sets of pulleys 1710 and 1714 such that a block-and-tackle type system is formed.

As shown, one end of the cable 720 may be coupled to a cable mounting plate 1818 of the camera mount 214. The cable mounting plate 1818 may be coupled to, for example, the camera support 712 (shown as transparent for the purposes of illustration). The cable mounting plate 1818 may include an opening for receiving at least a portion of the cable 720. Additionally, or alternatively, the cable 720 may be coupled to the camera mount 214 using for example, one or more of an adhesive, welding, and/or any other suitable form of coupling.

As shown, the fixed set of pulleys 1710 and the suspended set of pulleys 1714 each include three pulleys. However, such a configuration is non-limiting. For example, the fixed set of pulleys 1710 and the suspended set of pulleys 1714 may each include two, four, six, eight, or any other suitable number of pulleys. In some instances, the fixed set of pulleys 1710 and the suspended set of pulleys 1714 may each include a different number of pulleys.

The pulley system 1708 may provide a mechanical advantage. For example, the pulley system 1708 may cause the biasing mechanism 716 to experience a greater force than the force applied at the camera mount 214 by, for example, the interchangeable lens assembly 700 of FIG. 7. In some instances, the force experienced by the biasing mechanism 716 may be eight times greater than the force experienced by the camera mount 214. In other words, the pulley system 1708 may generally be described as a ⅛ ratio pulley system.

Further, as a result of the mechanical advantage of the pulley system 1708, a change in the length of the cable extending from the cable opening 1720 may be less than a change in the separation distance 1718. In other words, a magnitude of change in the separation distance 218 between the camera 212 and the mounting plate 202 is greater than a magnitude of change in the separation distance 1718 between the first and second pulley axes 1712 and 1716. Therefore, a magnitude of change in the force exerted by the biasing mechanism 716 is based, at least in part, on a magnitude of change in the separation distance 1718 between the first and second pulley axes 1712 and 1716 instead of a magnitude of change in the separation distance 218 between the camera 212 and the mounting plate 202. Therefore, in some instances, the biasing mechanism 716 may be generally described as causing the receptacle 708 to exert a substantially uniform (e.g., consistent and/or constant) force on the fitting 706 as the camera mount 214 moves along the track 220 relative to a situation where the pulley system 1708 is not used.

For example, assuming the pulley system 1708 is a ⅛ ratio pulley system, when the separation distance 218 between the camera 212 and the mounting plate 202 increases 1 cm the separation distance 1718 between the first and second pulley axes 1712 and 1716 may decrease by 0.125 cm. As such, a change in the magnitude of the force exerted by the receptacle 708 on the fitting 706 of the interchangeable lens assembly 700 of FIG. 7 is less than the situation where the biasing mechanism 716 is not coupled to the pulley system 1708.

As also shown in FIG. 18, the one or more stops 718 are positioned at opposing longitudinal ends of the track 220. As such, the camera mount 214 may be prevented from disengaging the track 220 in response to longitudinal movement. Further, the track 220 may include one or more recesses 1820 extending longitudinally along the track 220. The one or more recesses 1820 may engage the one or more protrusions 1208 extending from the groove 1202 of the camera mount base 710. As such, the camera mount 214 may be prevented from disengaging the track 220 along a vertical axis 1822.

In FIG. 18, the camera mount 214 is schematically illustrated with one or more transparent components for the purposes of clarity and not by way of limitation. Further, some features of the camera mount 214 (e.g., the camera clamp 714) are omitted from the illustration of the camera mount 214 shown in FIG. 18 for the purposes of clarity and not by way of limitation.

According to one aspect of the disclosure, there is provided a mounting assembly for an optical video system. The mounting assembly for the optical video system may include a platform having a track extending longitudinally along the platform. A camera mount may be slideably coupled to the track. A camera may be coupled to the camera mount. The camera may include a receptacle for engaging an interchangeable lens assembly. The mounting assembly for the optical video system may also include a biasing mechanism, wherein the biasing mechanism urges the camera mount along the track such that the receptacle engages the interchangeable lens assembly.

According to another aspect of the disclosure, there is provided a mounting assembly for an optical video system. The mounting assembly for the optical video system may include a platform having a top surface and a bottom surface, the top surface being opposite the bottom surface. A track may be coupled to the top surface and extend longitudinally along the platform. A camera mount may be slideably coupled to the track. A camera may be coupled to the camera mount. The camera may include a receptacle for engaging an interchangeable lens assembly. The mounting assembly for the optical video system may also include a biasing mechanism for urging the camera mount along the track. A first end of the biasing mechanism may be coupled to the bottom surface of the platform and a second end of the biasing mechanism may be coupled to a pulley system. The pulley system may include a fixed set of pulleys, the fixed set of pulleys being coupled to the bottom surface of the platform, and a suspended set of pulleys, the suspended set of pulleys being coupled to the second end of the biasing mechanism. The suspended set of pulleys may be moveable relative to the bottom surface of the platform. A cable may extend around each pulley of the suspended set of pulleys and each pulley of the fixed set of pulleys. One end of the cable may be coupled to the camera mount.

According to yet another aspect of the disclosure, there is provided a video measurement platform system. The video measurement platform system may include a stage for supporting a manufactured part. The stage may be capable of movement in multiple axes. The video measurement platform system may also include a mounting assembly for an optical video system. The mounting assembly may include a platform having a top surface and a bottom surface, the top surface being opposite the bottom surface. A track may be coupled to the top surface and extend longitudinally along the platform. A camera mount may be slideably coupled to the track. A camera may be coupled to the camera mount. The camera may include a receptacle for engaging an interchangeable lens assembly. A mounting plate may be coupled to a longitudinal end of the mounting assembly. The mounting plate may include a flange member. The flange member may define a passageway for receiving the interchangeable lens assembly. The flange member may include at least one longitudinal groove. The longitudinal groove may extend into a transverse slot. The mounting assembly may also include a biasing mechanism for urging the camera mount along the track. A first end of the biasing mechanism may be coupled to the bottom surface of the platform and a second end of the biasing mechanism may be coupled to a pulley system. The pulley system may include a fixed set of pulleys, the fixed set of pulleys being coupled to the bottom surface of the platform, and a suspended set of pulleys, the suspended set of pulleys being coupled to the second end of the biasing mechanism. The suspended set of pulleys may be moveable relative to the bottom surface of the platform. A cable may extend around each pulley of the suspended set of pulleys and each pulley of the fixed set of pulleys. One end of the cable may be coupled to the camera mount.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

What is claimed is:

1. A mounting assembly for an optical video system comprising:
    a platform having a track extending longitudinally along the platform;
    a camera mount slideably coupled to the track;
    a camera coupled to the camera mount, the camera including a receptacle for engaging an interchangeable lens assembly;
    a biasing mechanism, wherein the biasing mechanism urges the camera mount along the track such that the receptacle engages the interchangeable lens assembly; and
    a mounting plate coupled to the platform at a longitudinal end of the mounting assembly, wherein the mounting plate includes a flange member, the flange member defining a passageway for receiving the interchangeable lens assembly, the passageway extending through the mounting plate.

2. The mounting assembly of claim 1, wherein the biasing mechanism is positioned on a bottom surface of the platform and the track is coupled to a top surface of the platform, the bottom surface being opposite the top surface.

3. The mounting assembly of claim 2, wherein a first end of the biasing mechanism is coupled to the platform and a second end of the biasing mechanism is coupled to a pulley system.

4. The mounting assembly of claim 3, wherein the pulley system includes a suspended set of pulleys and a fixed set of pulleys, the suspended set of pulleys being movable relative to the bottom surface of the platform and the fixed set of pulleys being coupled to the bottom surface of the platform.

5. The mounting assembly of claim 4, wherein a cable extends around each pulley of the suspended set of pulleys and each pulley of the fixed set of pulleys.

6. The mounting assembly of claim 5, wherein one end of the cable is coupled to the camera mount.

7. The mounting assembly of claim 6, wherein the platform includes a cable opening, the cable opening including an additional pulley, wherein the cable extends through the cable opening and around the additional pulley.

8. The mounting assembly of claim 1, wherein the flange member includes at least one longitudinal groove, the longitudinal groove extending into a transverse slot.

9. The mounting assembly of claim 8, wherein the longitudinal groove and the transverse slot collectively define a portion of a bayonet coupling.

10. A mounting assembly for an optical video system comprising:
    a platform having a top surface and a bottom surface, the top surface being opposite the bottom surface;
    a track coupled to the top surface and extending longitudinally along the platform;
    a camera mount slideably coupled to the track;
    a camera coupled to the camera mount, the camera including a receptacle for engaging an interchangeable lens assembly; and
    a biasing mechanism for urging the camera mount along the track, wherein a first end of the biasing mechanism is coupled to the bottom surface of the platform and a second end of the biasing mechanism is coupled to a pulley system, the pulley system including:
        a fixed set of pulleys, the fixed set of pulleys being coupled to the bottom surface of the platform;
        a suspended set of pulleys, the suspended set of pulleys being coupled to the second end of the biasing mechanism, wherein the suspended set of pulleys are moveable relative to the bottom surface of the platform; and
        a cable extending around each pulley of the suspended set of pulleys and each pulley of the fixed set of pulleys, wherein one end of the cable is coupled to the camera mount.

11. The mounting assembly of claim 10, wherein the platform includes a cable opening, the cable opening including an additional pulley, wherein the cable extends through the cable opening and around the additional pulley.

12. The mounting assembly of claim 10, further comprising a mounting plate coupled to the platform at a longitudinal end of the mounting assembly.

13. The mounting assembly of claim 12, wherein the mounting plate includes a flange member, the flange member defining a passageway for receiving the interchangeable lens assembly, the passageway extending through the mounting plate.

14. The mounting assembly of claim 13, wherein the flange member includes at least one longitudinal groove, the longitudinal groove extending into a transverse slot.

15. The mounting assembly of claim 14, wherein the longitudinal groove and the transverse slot collectively define a portion of a bayonet coupling.

16. A video measurement platform system comprising:
    a stage for supporting a manufactured part, the stage being capable of movement in multiple axes; and
    a mounting assembly for an optical video system, the mounting assembly including:
        a platform having a top surface and a bottom surface, the top surface being opposite the bottom surface;
        a track coupled to the top surface and extending longitudinally along the platform;
        a camera mount slideably coupled to the track;
        a camera coupled to the camera mount, the camera including a receptacle for engaging an interchangeable lens assembly;
        a mounting plate coupled to a longitudinal end of the mounting assembly, wherein the mounting plate includes a flange member, the flange member defining a passageway for receiving the interchangeable lens assembly, wherein the flange member includes at least one longitudinal groove, the longitudinal groove extending into a transverse slot; and
        a biasing mechanism for urging the camera mount along the track, wherein a first end of the biasing mechanism is coupled to the bottom surface of the platform and a second end of the biasing mechanism is coupled to a pulley system, the pulley system including:
- a fixed set of pulleys, the fixed set of pulleys being coupled to the bottom surface of the platform;
- a suspended set of pulleys, the suspended set of pulleys being coupled to the second end of the biasing mechanism, wherein the suspended set of pulleys are moveable relative to the bottom surface of the platform; and
- a cable extending around each pulley of the suspended set of pulleys and each pulley of the fixed set of pulleys, wherein one end of the cable is coupled to the camera mount.

17. The video measurement platform system of claim 16, wherein the longitudinal groove and the transverse slot collectively define a portion of a bayonet coupling.

18. The video measurement platform system of claim 16, wherein the platform includes a cable opening, the cable opening including an additional pulley, wherein the cable extends through the cable opening and around the additional pulley.

* * * * *